United States Patent [19]
Shah

[11] Patent Number: 6,156,295
[45] Date of Patent: Dec. 5, 2000

[54] HEAT-SAFE HAIR PREPARATION AND METHOD OF USING SAME

[75] Inventor: Snehal M. Shah, Artesia, Calif.

[73] Assignee: Neutrogena Corporation, Los Angeles, Calif.

[21] Appl. No.: 08/240,862

[22] Filed: May 10, 1994

[51] Int. Cl.[7] ............................... A61K 7/06; A61K 9/00
[52] U.S. Cl. .................. 424/47; 424/70.1; 424/70.13; 424/70.14
[58] Field of Search ................ 424/74, 70, 195.1, 424/70.13, 70.14, 47

[56] References Cited

U.S. PATENT DOCUMENTS

| | | | |
|---|---|---|---|
| 4,705,681 | 11/1987 | Maes | 424/70 |
| 5,041,285 | 8/1991 | Lundmark | 424/70 |
| 5,217,711 | 6/1993 | De Oliveira | 424/70 |
| 5,227,164 | 7/1993 | Lundmark | 424/401 |
| 5,348,737 | 9/1994 | Syed | 424/71 |

OTHER PUBLICATIONS

Brooks Industries inc. "Plant Proteins" Cosmetic Ingredients and Ideas Spring 1992.

*Primary Examiner*—Thurman K. Page
*Assistant Examiner*—P. McQueeney
*Attorney, Agent, or Firm*—Richard R. Mybeck; Peter B. Scull

[57] ABSTRACT

The present invention relates a hair treatment preparation which, in conjunction with after-applied heat, such as normal blow-drying, adds strength to, and repairs damage to, bleached and permed hair and enhances moisture retention. The treatment preparation consists of an aqueous blend of a hydrolyzed wheat protein and wheat oligosaccharides, wheat amino acids, and panthenol, as its essential active ingredients, with or without selected additives such as panthenyl ethyl ether, fragrance, preservatives, and the like. The invention also discloses a method of strengthening and repairing damaged hair comprising applying the hair treatment hair preparation of the present invention onto damaged hair, and thereafter drying the treated hair. Certain aspects of hair strength, especially for previously permed hair, appear to be increased when the thus treated hair is blow-dried.

12 Claims, No Drawings

HEAT-SAFE HAIR PREPARATION AND METHOD OF USING SAME

INTRODUCTION

This invention relates generally to the field of hair conditioning and more particularly, to a hair treatment preparation which, when sprayed or otherwise applied to human hair, exhibits both high moisture retention and hair strengthening while preventing further damage to hair resulting from the excessive use of heated hair styling equipment, coarse brushes, chemical treatments, and the like.

BACKGROUND OF THE INVENTION

While vanity, grooming, and pride in appearance are important traits, not necessarily limited to humans, the grooming of the human hair is an important daily activity for many people and has indeed, been so for a very long time. What has been recognized for a much shorter period of time is that substantially all of the currently practiced hair grooming techniques, albeit they improve appearance, actually damage human hair to some extent. In particular, the act of blow-drying, or otherwise heat treating hair is conventionally believed to damage hair. Often this damage will require more grooming in an ultimately futile attempt to improve the perceived appearance of the hair. An illustrative example of this sequence occurs when a person attempts to change the curliness, or waviness, of his/her hair.

By way of background, it should be noted that the hair is a special arrangement of hard keratin which develops by the reproduction of cells from the germinal distinctive structures known as follicles. As the cells move up the follicle, toward the skin surface, the amino acids (building blocks of all protein) contained therein join together to create the principal three components of the hair fiber. On close examination of the visible part of the hair fiber, it is found that these components or parts are arranged into three separate and distinct layers namely, the cuticle, the cortex, and the medulla.

The cuticle is the layer on the outside of the hair shaft. It consists of hard, flattened, horny scales which overlap one another to the extent that five to seven scales are found in the length of one scale. In other words, at any point along the hair shaft the cuticle can be as many as seven scales in thickness, however, extreme cases have been found with as many as eleven layers. This gives a very strong, flexible arrangement, similar to that of the scales of a fish. The cuticle layer permits the waving of hair, but does not, by any means, cause this waving by itself.

The free ends of these overlapping, sloping, flat scales (called imbrications) point upwards and outwards in the direction of hair growth. If a strand of hair is rubbed lengthwise between the finger and thumb, the fingers will slide freely in the direction of the hair ends. This is because the imbrications, pointing toward the tip of the hair, facilitate movement in that direction. Greater resistance is encountered when attempting to slide the fingers toward the root. The arrangement of protruding scaly edges also allows for the easy removal, by brushing of undesirable material such as flaking skin or scalp cells, dirt particles, etc., which otherwise would accumulate on the scalp surface.

The function of the cuticle is to protect the more delicate cortex from injury. If the cuticle is damaged by excessive bleaching, permanent wave solutions or harsh chemicals, the cortex is exposed to injury. If steps are not taken to avoid further damage to the cuticle, the cortex could be destroyed or weakened. The cuticle is unusually resistant to chemical breakdown, but it cannot withstand careless treatment.

At the ends or tips of the hair shaft the cuticle is often dislodged or broken away. The cortex is thus open to the drying effects of air, leading to frayed and split ends, which look unsightly and ragged. For this reason alone, it is advisable to keep the hair trimmed in an effort to prevent this type of cuticle damage to the hair.

The cuticle scales act as tiny reservoirs in which the supply of sebum is maintained. If the cuticle was smooth, this vital oil would be easily washed or rubbed off. The natural sheen of healthy hair is primarily due to this coating of sebum on the cuticle and its complete loss could cause hair to become dull and drab.

Because of the projecting nature of the scales and their oil coating, the scales catch much dirt, debris, broken scales and other foreign matter. Frequent shampooing is necessary to keep the hair clean and hygienic. Removal of excess oils and dirt assists the proper penetration of permanent wave solutions, tints, or other hair products into the cortex. The cuticle is also used as a base for the deposit of hair sprays, lacquers, conditioners, fillers and other hair cosmetics.

The type of cuticle scales can vary widely from loose, open sales to tight, firm scales. The degree of porosity depends, to a large extent, on the nature of the cuticle surface. Whether the hair is porous or resistant depends on the type of cuticle it has.

The cortex is the most important layer of the hair and makes up from 75% to 90% of its bulk. In fact, it may be said that practically all the well-known behavior of human hair is due to this most important layer.

The physical properties of the hair which depend upon the cortex are: strength, elasticity, pliability, direction and manner of growth, size or diameter, texture and quality. The natural color of the hair is due to the pigment in the cortex. For a natural looking tint, it is necessary therefore to get cosmetic coloring matter into this layer.

The natural wave of the hair comes from physical changes in the cortex. These changes take place in the follicle before the hair is fully developed. Permanent waving, on the other hand, involves chemically induced changes in the cortex of mature hair. Curling, and all forms of hairstyling, depend for their results on artificial alternations to the structure of the cortex.

The physical structure of the cortex is very complicated. It is made of many millions of parallel fibers of hard keratin, often referred to as polypeptide chains. These parallel fibers are twisted around one another, something very much like heavy rope in appearance.

Because of the nature of the cortex, it gives the hair great strength and elasticity. In fact, it is claimed that human hair is stronger than copper wire of the same diameter. A single strand of hair, in good condition, will support a weight of approximately 5 to 7 ozs. The rate and direction of growth of hair is controlled by cell division at the papilla in the follicle.

At no other stage in history has the condition of the hair in the community been worse than it is today. Many unthinking and untrained persons try to do things to their hair for which it is wholly unsuited. Materials are available to supply the whims of everyone who desires changes in the hair. However, knowledge is required to insure their proper application and usage and to avoid a breakdown in the basic hair structure. The practitioner must know what can be done and what must not be done to the cortex and cuticle of the hair if permanent damage is to be avoided. It is the proper application of professional knowledge and skill which will help to eliminate or minimize damage to or loss of hair.

The medulla is the middle layer of the hair. It is made up of a column of cells, two or four rows wide. The medulla is not always a continuous part of the hair but it is frequently broken or even entirely absent from the hair shaft. This condition is often found in hair and it is suspected that the state of health and the taking of certain medicines has a direct bearing on its absence.

The purpose or function of the medulla is unknown. Hair does not seem to suffer when it is missing. It is made of soft keratin, whereas the cuticle and cortex are formed of hard keratin. Pigment of the hair is often found in this layer as well.

An understanding of the two main parts of the hair the cortex and the cuticle and their basic differences, that is, each layer performs separate and distinct functions is important to a clear understanding of the present invention. These distinctions in function have resulted in the separation into two structures which are composed of different arrangements of hard keratin. In the case of the hair we have a fine example of a biological marvel known as the "division of labor."

In other prior art approaches, Maes et al. U.S. Pat. No. 4,705,681 teach that a formulation of d-panthenyl ethyl ether and d-panthenol in a 9:1 ratio can be used to decrease the friction between hairs and facilitate the combing and brushing of hair treated by the formulation. Hair treated with this formula exhibits decreased damage, due to decreased hair friction. Newell et al., U.S. Pat. No. 4,970,067 discloses another attempt to mitigate the harm of perming and the like by the application of a carrier containing an amino acid and protein.

Finally, Lundmark, U.S. Pat. No. 5,041,285 teaches the application of a mixture of alantoin, panthenol and alcohol to the hair followed by heat.

As appears from the above, there is no known formulation or method in the prior art by which a hair treatment preparation is employed to repair damaged hair, while exhibiting high moisture retention and strengthening of hair. Further, none are able to use the heat of blow-drying to repair damaged hair, or exhibit high moisture retention and the strengthening of hair.

In general, the permanent waving of human hair involves, inter alia, the application of harsh solutions and intense heat, all of which has the propensity to damage both hard and soft keratin and impair the quality of the hair. Other treatments, such as bleaching and the like are also prone to deleteriously affect the quality of the hair.

Accordingly, a real need exists for something which can somehow counteract or defend against the adverse effects of conventional hair treatments and manipulation and even, if possible, coact with the adverse factors to create a beneficial effect for the hair being treated. It is toward the resolution of this need that the present invention is directed.

BRIEF SUMMARY OF THE INVENTION

The subject invention relates generally to hair care and more particularly to a hair treatment preparation which exhibits both high moisture retention and hair strengthening while preventing further damage to hair from the excessive use of either heat styling equipment or mechanical styling equipment. The formulation of the present invention is especially effective when used on hair that is chemically treated and thus damaged or weakened and utilizes the application of heat to strengthen such hair. The subject invention achieves these unexpected results with a new and unique formulation comprising a unique mixture of hydrolyzed wheat protein and oligosaccharides with wheat amino acids and panthenol, with or without panthenyl ethyl ether, combined with the proper set of preservatives. The formulation may be delivered by means of a spray delivery forms and can be rapidly dried. Further, it will be demonstrated that this composition can actually repair damaged hair when used in conjunction with blow-drying.

Accordingly, a primary object of the present invention is to provide a novel and unique hair treatment preparation delivered in a spray form which provides both high moisture retention in and strengthening of the hair and prevents damage heretofore associated with excessive use of heated hair styling equipment.

Another object of the present invention is to provide a novel and unique hair treatment preparation in a spray form which increases the strength of previously damaged hair.

These and still further objects, as shall hereinafter appear, are readily fulfilled by the present invention in a remarkably unexpected manner as will be readily discerned from the following detailed description of an exemplary embodiment thereof.

DESCRIPTION OF THE PREFERRED EMBODIMENT

The present invention comprises a unique mixture of ingredients which yields a remarkably effective hair treatment preparation that enables human hair to be strengthened by blow-drying after it has been treated with the formulation of the subject invention.

More particularly, the present invention relates to a novel hair care preparation which enhances the moisture content of the hair, especially chemically damaged hair, while simultaneously strengthening the hair and rendering it resistant to further damage from the use of heated styling equipment such as dryers and the like.

The unexpected benefit attained by the preparation of the present invention is the result of a synergistic coaction between strategic amounts of hydrolyzed wheat protein and wheat oligosaccharides (available from Croda, Inc., Parsippany, N.J. under the tradename CROPEPTIDE W), wheat amino acids, and panthenol in a water carrier.

Thus, the essential components of the hair preparation embodying the present invention are preferably disposed in a water carrier and comprise, hydrolyzed wheat protein and wheat oligosaccharides, wheat amino acids, and panthenol. Panthenyl ethyl ether, polysorbate 20, (or known equivalent), preservatives, tetrasodium EDTA, sodium polystyrene sulfonate, glycerin and fragrance in the range shown in Table I can be added as desired. The hydrolyzed wheat protein and wheat oligosaccharides will generally comprise from about 2.5% to about 5% (W/W) of the total formulation while the wheat amino acids comprise from about 0.2 to about 1% (W/W) and panthenol makes up from about 0.5% to about 2% (W/W). Panthenyl ethyl ether consists of about 0% up to about 0.25% (W/W) and water makes up the balance, usually from about 83% to about 96% (W/W) of the total formulation. Preservatives, such as DMDM hydantoin, phenoxyethanol and methylparaben and the known equivalents thereto, tetrasodium EDTA, glycerine and fragrance can be added as desired, as shown in Table I.

TABLE I

| Raw Material | From: | To: |
|---|---|---|
| Water | 96.03 | 83.8 |
| Hydrolyzed Wheat Protein and Wheat Oligosaccharides | 2.50 | 5.00 |
| Wheat Amino Acids | 0.20 | 1.00 |
| Panthenol | 0.50 | 2.00 |
| Panthenyl Ethyl Ether | 0.00 | .25 |
| Polysorbate 20 | 0.20 | 0.50 |
| Preservatives | | |
| DMDM Hydantoin | 0.20 | 0.50 |
| Phenoxyethanol | 0.20 | 0.50 |
| Methylparaben | 0.05 | 0.20 |
| Tetrasodium EDTA | 0.02 | 0.05 |
| Fragrance | 0.10 | 0.20 |
| Glycerin | 0.00 | 4.00 |
| Sodium Polystyrene Sulfonate | 0.00 | 2.00 |
| TOTAL: | 100.00% | 100.00% |

The ranges in weight percent of the cosmetically active ingredient relative to each other in a preferred practice of the present invention are shown in Table II.

TABLE II

| Raw Material | From: | TO: |
|---|---|---|
| Hydrolyzed Wheat Protein and Wheat Oligosaccharides | 78.1 | 60.6 |
| Wheat Amino Acids | 6.3 | 12.1 |
| Panthenol | 15.6 | 24.3 |
| Panthenyl Ethyl Ether | 0.00 | 3.0 |
| TOTAL: | 100.0% | 100.0% |

In one practice of the present invention, the active ingredients are combined (in weight percent) to provide about 15.6% to about 24.3% panthenol, from about zero to about 3.0% of panthenyl ethyl ether; from about 6.3%–12.1% of wheat amino acids and from about 78.1% to about 60.6% of hydrolyzed wheat protein and wheat oligosaccharides.

These main ingredients and the perceived function each serves will now be described. The hydrolyzed wheat protein and wheat oligosaccharides work as a moisture regulator in hair and increases hair elasticity (relieves hair stress resulted from stiffening of hair fiber) Moisture regulation means making hair less brittle at lower RH (relative humidity) and making hair less limp at high RH. Also, it has been found that the hair becomes less prone to mechanical damage-breakage. These features are especially important to damaged hair, as the hair is vulnerable to even normal brushing, combing or heat styling equipment.

Wheat amino acids with a molecular weight of 150 exhibit powerful moisture binding properties, retaining up to four times its weight in moisture at high humidity. Increased moisture provides damaged hair with much needed suppleness, gloss and softness. Amino acids in the formulation of the present invention have been found to penetrate inside hair.

Panthenol penetrates into the cortex and provides long lasting moisture retention and this ability will prevent excessive drying of hair when heat styling equipment are used. Also it has been found that panthenol increases tensile strength of hair providing strength to hair. Once inside the hair shaft, panthenol is retained in hair over several shampooings.

The optional panthenyl ethyl ether also provides enhanced moisture retention and also penetrates deep into the hair. The optional sodium polystyrene sulfonate, a high molecular weight polymer, helps prevent fly-away, yet adds body for better manageability, enhanced lubricity and wet combing which is essential for damaged fine, thin hair.

The ratio (by weight) of panthenol to hydrolyzed wheat protein and wheat oligosaccharides ranges from about 1:5 to about 2:5. The ratio (by weight) of wheat amino acids to hydrolyzed wheat protein and wheat oligosaccharides ranges from about 2:25 to about 1:5. The corresponding ratio (by weight) to hydrolyzed wheat protein and wheat oligosaccharides for panthenyl ethyl ether, to hydrolyzed wheat protein oligosaccharides when used will range from about 0:25 to about 1:20.

A subtle key to obtaining a practical consumer-friendly product, that is, a product which does not have an objectionable odor or smell, is to employ an acceptable set of preservatives which do not possess an unpleasant smell. The preservatives listed herein are believed to be the only presently available preservatives which provide an acceptable odor for the product. It is of course understood that should additional preservatives be developed having an unobjectionable odor, they likewise are suitable for incorporation into the present invention.

The unique effects obtained by the practice of the present invention can be seen from reference to the examples shown below. For instance, in Example 1, blow-drying substantially augments the percentage increase in hair strength experienced by damaged hair, i.e. hair that has been bleached or permed. The composition of the subject invention therefore changes, the practical necessity of the blow-drying hair, from a negative to a positive factor.

As shown in Example 2, after one treatment cycle for permed hair, the subject invention increased moisture retention by 41.7% and 46.5% for air dried and blow dried hair, respectively, compared to control group hair.

The most surprising effect demonstrated by the subject invention was that the repeated use of the product, along with blow drying, actually strengthened and repaired damaged hair. This was determined by testing an appropriate sample of the novel formulation of the present invention in the following manner. A test was set up using hair samples (undamaged virgin hair and damaged bleached hair) of approximately 20 cm in length. Prior to the experiment, these hair were stored at constant temperature (20° C.) and constant relative humidity (15% RH). Hair strength was measured using the following observations. Hair, upon extension with increasing forces, passes through three phases. The first phase (the elastic region) is characterized by reversible extension. The second phase is the yield region, characterized by an irreversible transformation in which covalent bonds are probably broken. Finally, the third phase corresponds to the breaking point, that is, where complete fiber breakage occurs. Thus, the yield region is the one most likely to correlate with covalent and disulfide bond breakage in hair, (i.e., overall hair damage), and therefore, evaluating the yield slope can provide a measurement of hair damage.

In the laboratory, a custom designed tensile strength tester was used to assess the stress-strain behavior of hair. For this, a single strand of hair of 20 cm long was extended with a force at 20 gm load setting at a speed of 100 mm/minute. The slope of the yield region which correlates with covalent and disulfide bond breakage (i.e., overall hair damage) was measured for each hair.

For each control or treatment group, 10 strands of hair were measured and the mean yield slope was calculated for each and used to reflect the extent of hair damage. Thereafter, the viscoelastic properties of the human hair (i.e., its pliability or softness) was correlated directly with its moisture content. Routinely, the effects of various treatments on the biomechanical properties of hair are measured by a procedure that utilizes a Gas Bearing Electrodynamometer (GBE). In this technique, the increase in hair pliability induced by water is measured vs. time, as hairs are allowed to equilibrate back at ambient temperature and RH. The integrated area under the curve that depicts "% softening vs. time" for a given treatment is compared to that obtained with untreated hair and the results are expressed as "% Change After Treatment". A POSITIVE value for this comparison reflects an increase in overall hair softness (and manageability) because of a greater ability to retain moisture. On the other hand, a NEGATIVE value for this comparison indicates stiffening of the hair (and, therefore, a propensity for breakage), reflecting a loss in moisture holding ability. (See: R. A. Wall, L. D. Hunter, *Normal Adult Hair Cosmetics and Perfumery*, 89, February 1974); and G. C. Wood, The relaxation of Human Hair, *J. Textile Institute*, 45, pg 462–471,(1954))

To better understand the present invention, and not by way of limitation, the following examples are offered.

EXAMPLE 1

An experimental hair product containing 0.5 percent wheat amino acids, 4.0 percent hydrolyzed wheat protein and wheat oligosaccharides, 1.0 percent panthenol, 0.3 percent polysorbate 20, 0.7 percent preservatives and q.s. water was supplied for testing.

Hair samples (undamaged virgin hair and damaged bleached hair) of approximately 20 cm in length were selected. Prior to the conduct of the test, the hairs were stored at a constant temperature of 20° C. and at a relative humidity of 15% relative humidity ("RH").

Hair, upon extension with increasing forces, passes through three phases. The first phase (the elastic region) is characterized by reversible extension. The second phase is the yield region, characterized by an irreversible transformation in which covalent bonds are probably broken. Finally, the third phase corresponds to the breaking point, where complete fiber breakage occurs. Thus, the yield region is the one most likely to correlate with covalent and disulfide bond breakage in hair, (i.e., overall hair damage), and therefore, evaluating the yield slope can provide a measurement of hair damage.

In the laboratory, a custom designed tensile strength tester was used to assess the stress-strain behavior of hair. For this, a single strand of hair of 20 cm long was extended with a force at 20 gm load setting at a speed of 100 mm/minute. The slope of the yield region which correlates with covalent and disulfide bond breakage (i.e., overall hair damage) was measured for each hair.

For each control or treatment group, 10 strands of hair were measured and the mean yield slope was calculated and used to reflect the extent of hair damage.

The viscoelastic properties of human hair (i.e., its pliability or softness) correlate directly with its moisture content. Routinely, the effects of various treatments on the biomechanical properties of hair are measured by a procedure that utilizes a Gas Bearing Electrodynamometer (GBE). In this technique, the increase in hair pliability induced by water is measured vs. time, as hairs are allowed to equilibrate back at ambient temperature and RH. The integrated area under the curve that depicts "% softening vs. time" for a given treatment is compared to that obtained with untreated hair and the results are expressed as "% Change After Treatment".

Thus, a POSITIVE value reflects an increase in overall hair softness (and manageability) due to a greater ability to retain moisture. On the other hand, a NEGATIVE value indicates stiffening of the hair (and, therefore, a propensity to breakage), reflecting a loss in moisture holding ability.

The hair product described above was used in this study. Hair samples, both damaged and undamaged were first shampooed with REVLON FLEX shampoo, and then treated with the hair product defined above. Both products were applied by spraying a generous amount of the product onto hair, which was then lightly combed and excess product was removed by lightly wiping with tissue paper. Measurements were taken immediately after treatment. As always, the shampooed hair served as the untreated control. For multiple treatment, the shampoo plus treatment cycle was repeated five (5) times and measurements were taken after the last cycle.

For determining the effects of air and blow-drying, the treated or untreated hair was either air dried for three (3) minutes or dried with a professional salon hair dryer at normal temperature setting for one (1) minute and measurements were taken immediately after drying. At least ten (10) hair samples per group were used for measurements.

Changes in hair strength as affected by various treatments are summarized in Table IV also shown below.

The data can be interpreted as follows: bleached and permed hair show a much lower yield slope which is indicative of greater hair damage; the Revlon FLEX shampoo treatment, either at one cycle or five cycles, did not cause any changes in hair damage in any hair-types and therefore served as an inert control treatment; the formulation embodying the present invention is clearly shown to be highly effective in increasing hair strength and its overall effect on all three hair types was superior and more effective in strengthening damaged hair than undamaged virgin hair, and induced greater hair repair with multiple treatment.

The modifications which occur during the stretching of hair fibers within the range of elasticity (small pulling force) were shown to be highly dependent on the water content of hair, which directly affects hydrogen bonding and ionic interactions between hair keratin. Thus, product treatment which will maintain a high hair moisture content should soften hair and resulting in an overall improvement in the manageability of hair. Consequently, the integrated hair softening as an assessment of the moisture retention properties of hair has been utilized in this study.

The results obtained by these tests can be summarized as follows:

1. Damaged hair (bleached and permed) has a much lower moisture retention index than virgin hair, mainly due to its damaged keratin structure and cuticle layers which are highly susceptible to high water loss.

2. The shampoo control treatment was shown to induce a slight drying effect on all three types of hair. This drying effect increased slightly with blow-drying and with multiple treatment.

3. The tested product was shown to provide excellent moisture retention to all hair types. Again, multiple treatment resulted in a higher Moisture Retention Index.

The following results were obtained.

TABLE III

% INCREASE IN HAIR STRENGTH*

|  |  | TEST FORMULA | | |
|---|---|---|---|---|
|  |  | VIRGIN | BLEACHED | PERMED |
| One Cycle | Air-Dried | 12.3% | 17.3% | 20.2% |
|  | Blow-Dried | 15.0% | 21.7% | 38.8% |
| Five Cycle | Air-Dried | 19.2% | 25.5% | 30.8% |
|  | Blow-Dried | 17.7% | 31.7% | 35.2% |

*Averaged values of ten hair measurements

EXAMPLE 2

Hair was treated in accordance with the general procedures set forth in Example 1. The following results were obtained.

Effects of Hair Treatment Product on the Moisture Retention Properties of Hair

PERCENT INCREASE IN MOISTURE RETENTION

|  |  | VIRGIN | BLEACHED | PERMED |
|---|---|---|---|---|
| One Cycle | Air-Dried | 66.3% | 42.6% | 41.7% |
|  | Blow-Dried | 72.3% | 58.8% | 46.5% |
| Five Cycle | Air-Dried | 79.3% | 76.7% | 68.6% |
|  | Blow-Dried | 81.7% | 87.1% | 69.6% |

*As compared to the control treatment group.

From the foregoing, it is readily apparent that a new and useful embodiment of the present invention has been herein described and illustrated which fulfills all of the aforestated objects in a remarkably unexpected fashion. It is, of course, understood that such modifications, alterations and adaptations as may readily occur to the artisan confronted with this disclosure are intended within the spirit of this disclosure which is limited only by the scope of the claims appended hereto.

Accordingly, what is claimed is:

1. A water-based hair preparation containing as its essential cosmetically active ingredients from about 78.1 to about 60.6 weight percent of hydrolyzed wheat protein and wheat oligosaccharide, from about 6.3 to about 12.1 weight percent of wheat amino acids, from about 15.6 to about 24.3 weight percent panthenol; and from about 0 to about 3 weight percent of panthenyl ethyl ether.

2. A hair treatment preparation according to claim 1 further containing water soluble preservatives and fragrance admixed therein.

3. A hair treatment preparation according to claim 1 in which the ratio of panthenyl ethyl ether to panthenol by weight ranges from about 0:5 to about 1:8.

4. A hair treatment preparation according to claim 1 in which the ratio of wheat amino acids to panthenol by weight ranges from about 2:5 to about 1:2.

5. A hair treatment preparation according to claim 1 in which the weight ratio of the wheat amino acids to the hydrolyzed wheat protein and wheat oligosaccharides ranges from about 1:19 to about 1:3.

6. A hair treatment preparation according to claim 1 in which the weight ratio of the panthenyl ethyl ether to the hydrolyzed wheat protein and wheat oligosaccharides ranges from about 0:25 to about 1:20.

7. A hair treatment preparation according to claim 2 containing a preservative selected from the group consisting of DMDM hydantoin, phenoxyethanol, methylparaben and mixtures.

8. A hair treatment preparation consisting essentially of the following ingredients in the following percentages (w/w):

| Material | From | To |
|---|---|---|
| Water | 96.03% | 83.80% |
| Hydrolyzed Wheat Protein and Wheat Oligosaccharides | 2.50% | 5.00% |
| Wheat Amino Acids | 0.20% | 1.00% |
| Panthenol | 0.50% | 2.00% |
| Panthenyl Ethyl Ether | 0.00% | 0.25% |
| Polysorbate 20 | 0.20% | 0.50% |
| Preservatives |  |  |
| DMDM Hydantoin | 0.20% | 0.50% |
| Phenoxyethanol | 0.20% | 0.50% |
| Methylparaben | 0.05% | 0.20% |
| Tetrasodium EDTA | 0.02% | 0.05% |
| Fragrance | 0.10% | 0.20% |
| Glycerin | 0.00% | 4.00% |
| Sodium Polystyrene Sulfonate | 0.00% | 2.00%. |

9. A method of moisturizing, strengthening and repairing damaged hair comprising: spraying said hair with a water-based hair preparation containing as its essential cosmetically active ingredients from about 78.1 to about 60.6 weight percent of hydrolyzed wheat protein and wheat oligosaccharide, from about 6.3 to about 12.1 weight percent of wheat amino acids, from about 15.6 to about 24.3 weight percent panthenol; and from about 0 to about 3 weight percent of panthenyl ethyl ether; and blow drying said sprayed hair.

10. A method according to claim 9 in which said hair treatment preparation consists essentially of the following ingredients in the following percentages (w/w):

| Material | To | From |
|---|---|---|
| Water | 96.03% | 83.80% |
| Hydrolyzed Wheat Protein and Wheat Oligosaccharides | 2.50% | 5.00% |
| Wheat Amino Acids | 0.20% | 1.00% |
| Panthenol | 0.50% | 2.00% |
| Panthenyl Ethyl Ether | 0.00% | 0.25% |
| Polysorbate 20 | 0.20% | 0.50% |
| Preservatives |  |  |
| DMDM Hydantoin | 0.20% | 0.50% |
| Phenoxyethanol | 0.20% | 0.50% |
| Methylparaben | 0.05% | 0.20% |
| Tetrasodium EDTA | 0.02% | 0.05% |
| Fragrance | 0.10% | 0.20% |
| Glycerin | 0.00% | 4.00% |
| Sodium Polystyrene Sulfonate | 0.00% | 2.00%. |

11. A method according to claim 9 in which said hair preparation further contains preservatives and fragrance admixed therein.

12. A method according to claim 11 in which said hair treatment preparation consists essentially of the following ingredients in the following percentages (w/w):

| Material | To | From |
|---|---|---|
| Water | 96.03% | 83.80% |
| Hydrolyzed Wheat Protein and Wheat Oligosaccharides | 2.50% | 5.00% |
| Wheat Amino Acids | 0.20% | 1.00% |
| Panthenol | 0.50% | 2.00% |
| Panthenyl Ethyl Ether | 0.00% | 0.25% |
| Polysorbate 20 | 0.20% | 0.50% |

-continued

| Material | To | From |
|---|---|---|
| Preservatives | | |
| DMDM Hydantoin | 0.20% | 0.50% |
| Phenoxyethanol | 0.20% | 0.50% |
| Methylparaben | 0.05% | 0.20% |
| Tetrasodium EDTA | 0.02% | 0.05% |
| Fragrance | 0.10% | 0.20% |
| Glycerin | 0.00% | 4.00% |
| Sodium Polystyrene Sulfonate | 0.00% | 2.00%. |

* * * * *